United States Patent [19]

Inoue et al.

[11] 4,311,856
[45] Jan. 19, 1982

[54] PROCESS FOR SYNTHESIZING UREA

[75] Inventors: Shigeru Inoue, Kamakura; Hiroshi Ono, Fujisawa; Akito Fukui, Inba; Haruyuki Morikawa, Chiba, all of Japan

[73] Assignees: Toyo Engineering Corp.; Mitsui Toatsu Chemicals, Inc., both of Tokyo, Japan

[21] Appl. No.: 221,816

[22] Filed: Dec. 31, 1980

[51] Int. Cl.$^3$ .......................................... C07C 126/02
[52] U.S. Cl. .......................................... 564/67; 55/53; 55/70; 564/68
[58] Field of Search ............................ 564/67, 68, 70

[56] References Cited

U.S. PATENT DOCUMENTS 3,691,729  9/1972  De Rooy et al. .................. 55/70

FOREIGN PATENT DOCUMENTS 1248639  8/1967  Fed. Rep. of Germany ........ 564/67
1541273  4/1968  France ............................... 564/67
49-13770  3/1974  Japan ................................ 564/67

OTHER PUBLICATIONS

Zardi et al, Recycle Carbamate via Ejector, "Hydrocarbon Processing", vol. 49, (No. 4), pp. 115–116 (1970).

*Primary Examiner*—John Doll
*Attorney, Agent, or Firm*—Fisher, Christen & Sabol

[57] ABSTRACT

An inert gas containing carbon dioxide and ammonia and separated from a urea synthesis effluent under urea synthesis pressures is brought into contact with an absorbent along with unreacted carbon dioxide and ammonia separated in high pressure distillation at a pressure of from 10 to 25 kg/cm$^2$ G to absorb substantially all of the carbon dioxide and the major portion of the ammonia, and is cooled to be separated from the resulting liquid ammonia and then is discharged. The inert gas can be treated with little or no danger of explosion by the above method.

5 Claims, 1 Drawing Figure

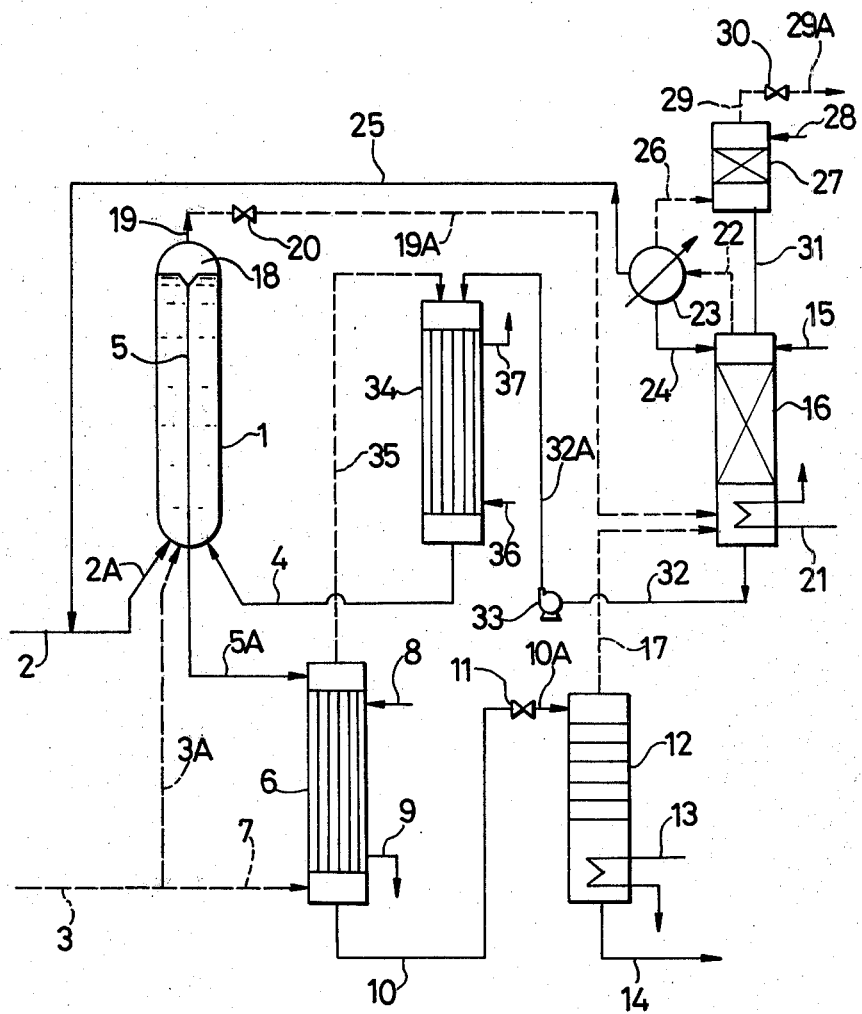

PROCESS FOR SYNTHESIZING UREA

BACKGROUND OF THE INVENTION

1. Field of the Invention

This invention relates to an improved cyclic urea synthesis process, in which urea is synthesized from carbon dioxide and ammonia in a stoichiometrical excess thereto.

2. Description of the Prior Art

Recently, separation of unreacted carbon dioxide and ammonia from a urea synthesis effluent in a urea synthesis process has been effected at more and more higher temperatures, and a typical example of the separation process is a stripping process with carbon dioxide gas or ammonia gas under urea synthesis pressures. In such a process as described above, inert gases contained in carbon dioxide and ammonia as starting materials such as nitrogen, hydrogen, and methane as well as a small amount of air added as a corrosion inhibitor in a urea synthesis autoclave (hereinafter referred to simply as an inert gas including the air) are accumulated in the steps operated at high pressures such as urea synthesis step, stripping step, or the like. Therefore, the inert gas is required to be withdrawn out of such steps.

There are two types of methods of withdrawing the inert gas, a first method in which the inert gas is separated in the urea synthesis autoclave, and a second method in which the inert gas is separated when unreacted carbon dioxide and ammonia stripped are condensed. The second method has such a drawback compared with the first method that the amount of carbon dioxide and ammonia entrained in the inert gas is increased.

Carbon dioxide and ammonia contained in the inert gas thus separated needs to be recovered. As one process for the recovery thereof, according to urea synthesis process of Snam Progetti S.P.A., the inert gas is separated on condensing unreacted carbon dioxide and ammonia stripped from the urea synthesis effluent with ammonia gas, and the inert gas thus separated is introduced into a medium pressure absorption column along with unreacted carbon dioxide and ammonia separated in medium pressure distillation to recover the carbon dioxide and ammonia contained in the inert gas ["Hydrocarbon Processing" 49 (No. 4) 115–116 (1970)].

As another process for the recovery thereof, according to a process of Stamicarbon N.V., an inert gas at the top of a urea synthesis autoclave is washed with an ammonium carbamate solution resulting from a low pressure carbon dioxide and ammonia recovery stage under urea synthesis pressures to absorb the carbon dioxide and ammonia contained therein, and the inert gas withdrawn from the absorption step is depressurized and then discharged (U.S. Pat. No. 3,691,729). It is necessary for this process to take an explosion-proof remedy because the inert gas, from which carbon dioxide and ammonia have been removed, has a danger of explosion, and to operate carefully because the process is performed under urea synthesis pressures and in an apparatus connected directly to the urea synthesis autoclave.

SUMMARY OF THE INVENTION

It is an object of this invention to provide a novel and improved cyclic urea synthesis process.

It is another object of this invention to provide an improved cyclic urea synthesis process including a novel method capable of treating an inert gas separated from a urea synthesis effluent with little or no danger of explosion.

According to this invention, the following urea synthesis process is provided:

A process for synthesizing urea which comprises reacting carbon dioxide and ammonia in a stoichiometrical excess thereto at urea synthesis pressures and temperatures to form a urea synthesis effluent containing unreacted carbon dioxide and ammonia, separating an inert gas from said urea synthesis effluent along with unreacted carbon dioxide and ammonia entrained in the inert gas under a pressure approximately equal to the urea synthesis pressures, subjecting said urea synthesis effluent to stripping with carbon dioxide or ammonia under a pressure approximately equal to the urea synthesis pressures to separate at least a part of said unreacted carbon dioxide and ammonia, subjecting the urea synthesis effluent resulting from said stripping to high pressure distillation under a pressure of from 10 to 25 $kg/cm^2$ gauge to separate the major portion of carbon dioxide and ammonia contained therein, subjecting the urea synthesis effluent resulting from said high pressure distillation to low pressure distillation to separate all of the carbon dioxide and ammonia contained therein to obtain an aqueous urea solution, producing urea from the aqueous urea solution thus obtained, contacting said inert gas separated along with unreacted carbon dioxide and ammonia entrained therein, as well as carbon dioxide and ammonia resulting from said high pressure distillation with an absorbent to absorb carbon dioxide and ammonia therein for forming a high pressure absorbate, cooling unabsorbed ammonia gas and said inert gas to separate resulting liquid ammonia from said inert gas, contacting said unreacted carbon dioxide and ammonia resulting from said stripping with said high pressure absorbate for condensation, and recycling an ammonium carbamate solution thus obtained and said liquid ammonia to said urea synthesis.

BRIEF DESCRIPTION OF THE INVENTION

The single FIGURE is a flow sheet for illustrating one embodiment of this invention.

DETAILED DESCRIPTION OF THE INVENTION

The process of the present invention is also applicable to a total recycle urea synthesis process, in which the carbon dioxide and ammonia resulting from the low pressure distillation are absorbed in the absorbent before hand.

The urea synthesis stage in the present invention is performed by use of ammonia in a stoichiometrical excess to carbon dioxide preferably at a temperature of from 170° to 220° C. and a pressure of from 100 to 300 $kg/cm^2$ G. The ammonia to carbon dioxide molar ratio is preferably of from 2.1 to 5, and most preferably of from 3 to 4.

The urea synthesis pressure is preferred to be as high as possible above an equilibrium pressure corresponding to the urea synthesis temperature. However, it is uneconomical to increase the urea synthesis pressure only because of decreasing the amount of carbon dioxide and ammonia entrained in the inert gas. Accordingly, the urea synthesis pressure is preferably selected from the above range.

According to the present invention, the inert gas is separated from the urea synthesis effluent under a pressure approximately equal to the urea synthesis pressure. The carbon dioxide and ammonia contained in the inert gas is desirably in an amount as low as possible. However, the partial pressure of carbon dioxide and ammonia over the urea synthesis effluent brought into contact with the inert gas is the lowest among respective stages operated under pressures approximately equal to the urea synthesis pressure. Therefore, it is the most advantageous to separate the inert gas from the urea synthesis effluent under a pressure approximately equal to the urea synthesis pressure. It is the most preferable to withdraw the inert gas from the top of the urea synthesis autoclave, but liquid-gas separator may be fitted between the urea synthesis stage and the urea synthesis effluent stripping stage thereby to separate the inert gas.

The term "a pressure approximately equal to the urea synthesis pressure" is meant to be used as "a pressure which is approximately equal to the urea synthesis pressure, or a pressure which is 10 kg/cm$^2$ thereabove at the most".

The urea synthesis effluent separated from the inert gas is subjected to stripping with carbon dioxide or ammonia under a pressure approximately equal to the urea synthesis pressure to separate at least a part of unreacted carbon dioxide and ammonia contained therein, wherein the temperature and pressure are preferably of from 150° to 230° C. and 90 to 310 kg/cm$^2$ gauge respectively. The carbon dioxide as starting material is preferably used as the gas for use in stripping because the degree of separation of unreacted carbon dioxide and ammonia is increased and because the solubility thereof in the urea synthesis effluent is low.

The urea synthesis effluent resulting from the stripping stage is depressurized to a pressure of from 10 to 25 kg/cm$^2$ gauge and introduced into the high pressure distillation stage to separate the major portion of unreacted carbon dioxide and ammonia. The temperature in the high pressure distillation stage is preferably in the range of from 110° to 170° C. The high pressure distillation stage may be of a rectification column, for example, a plate column having several stages, an apparatus composed of a heater and a liquid-gas separator, or other various apparatuses.

The urea synthesis effluent resulting from the high pressure distillation stage, which still contains a small amount of unreacted carbon dioxide and ammonia, is depressurized to a pressure of from 1 to 5 kg/cm$^2$ gauge to remove all of the unreacted carbon dioxide and ammonia, and a granular urea is obtained via a crystalline urea or urea melt in the finishing stage.

The carbon dioxide and ammonia separated from the aqueous urea solution at low pressures are absorbed in an appropriate absorbent such as water, aqueous ammonia, aqueous urea solution, and the like. The resulting absorbate is pressurized to the same pressure as in the high pressure distillation and brought into contact with carbon dioxide and ammonia separated in the high pressure distillation as well as the inert gas obtained by depressurizing the inert gas separated from the urea synthesis effluent to the same pressure as in the high pressure distillation to absorb all of the carbon dioxide and a part of the ammonia, wherein the temperature is preferably in the range of from 100° to 130° C. If the absorption pressure is increased above 25 kg/cm$^2$ gauge, both carbon dioxide and ammonia are absorbed with the result that the concentration of the inert gas is increased and consequently danger of explosion is also increased. Thus, the upper limit of the pressure in the high pressure distillation is restricted due to the danger of explosion of the inert gas, because the pressure in the high pressure distillation is to be the same as the absorption pressure of the carbon dioxide and ammonia separated in the high pressure distillation. On the other hand, the lower limit of the absorption pressure is restricted to be 10 kg/cm$^2$ gauge so that the amount of the absorbent may not become too much. The excess ammonia, which has not been absorbed in the absorption stage, is passed to the ammonia condensation stage along with the inert gas and cooled therein to separate the resulting liquid ammonia from the inert gas. A part of liquid ammonia thus obtained is recycled to the absorption stage for use in cooling, and the balance is recycled to the urea synthesis stage. The inert gas containing some amount of ammonia is further introduced into the washing column and washed with water or the like to remove ammonia.

The inert gas introduced into the washing column has no danger of explosion so long as the pressure is lower than 25 kg/cm$^2$ gauge, but has danger of explosion in a very short line during a period of ranging from the withdrawal of the inert gas from the washing column to the depressurizing thereof. However, the above line is under a relatively low pressure, and is connected to the main line of the process through the washing column, so that even if an explosion should occur therein, it would inflict no serious damage on the main line of the process.

The high pressure absorbate obtained by absorbing the carbon dioxide and ammonia separated in the high pressure distillation is pressurized to the pressure in the stripping stage, and is brought into contact with the carbon dioxide and ammonia separated in the stripping stage to condense and liquify at least a part of the carbon dioxide and ammonia while removing the heat of reaction so that the urea synthesis temperature may be at a predetermined level. The above condensation is effected at a temperature of from 140° to 200° C. while performing heat recovery by means of the production of steam having a pressure of from 3 to 10 kg/cm$^2$ gauge. The condensate thus obtained as well as uncondensed carbon dioxide and ammonia, if any, are recycled to the urea synthesis stage.

Specific embodiments of the present invention will be described hereinafter with reference to the accompanying drawing.

The make-up ammonia from line 2 is pressurized by a pump (not shown) along with recycled ammonia from line 25 and introduced through line 2A into the urea synthesis autoclave 1, the make-up carbon dioxide is pressurized by a compressor (not shown) and, as the case may be, a portion thereof is introduced thereinto through line 3A, and further the recovered ammonium carbamate solution as well as the uncondensed carbon dioxide and ammonia, if any, are introduced thereinto through line 4, so that the reaction may be conducted at a pressure of from 100 to 300 kg/cm$^2$ gauge and a temperature of from 170° to 220° C. The molar ratio of the total ammonia to the total carbon dioxide at the inlet of the urea synthesis autoclave 1 is preferably in the range of from 2.1 to 5, particularly 3 to 4. A discharge pipe 5 is formed so as to be provided in the urea synthesis autoclave, and an inert gas separation space 18 is also formed so as to be provided at the top of the urea synthesis autoclave.

The urea synthesis effluent is withdrawn from the discharge pipe 5 and introduced into the top of stripper 6 through line 5A. The stripper 6 is heated to a temperature of from 150° to 230° C. with a high pressure steam which is introduced from line 8 to and discharged from line 9. The pressure of the stripper is kept at a pressure approximately equal to the pressure in the urea synthesis autoclave ranging from 90 to 310 kg/cm$^2$ gauge. At least a portion of the make-up carbon dioxide from line 7 is introduced into the bottom of stripper 6, and is brought into countercurrent contact with the urea synthesis effluent to strip a portion of the unreacted carbon dioxide and ammonia in the urea synthesis effluent.

The urea synthesis effluent resulting from the stripper 6 is, via line 10, depressurized to 10–25 kg/cm$^2$ gauge by the reducing value 11, and is introduced into the top of high pressure distillation column 12 through line 10A. The heater 13 is fitted at the bottom of the high pressure distillation column to heat the urea synthesis effluent which has flown downward therethrough. The major portion of the unreacted carbon dioxide and ammonia, which remain in the urea synthesis effluent, is separated in the high pressure distillation column.

An aqueous urea solution, which still contains a small amount of unreacted carbon dioxide and ammonia, is withdrawn from the bottom of high pressure distillation column 12 through line 14, is depressurized to 1–5 kg/cm$^2$ gauge, and is passed for treatment to a low pressure unreacted carbon dioxide and ammonia separation stage (not shown) according to the conventional procedure to obtain an aqueous urea solution. Subsequently, the aqueous urea solution is passed to a conventional finishing stage to obtain a urea product.

The absorbate obtained by absorbing the carbon dioxide and ammonia separated in the low pressure unreacted carbon dioxide and ammonia separation stage in an absorbent is pressurized to 10–25 kg/cm$^2$ gauge, and is introduced into the top of high pressure absorber 16 through line 15. To the bottom of high pressure absorber 16, the unreacted carbon dioxide and ammonia separated in the high pressure distillation column 12 is introduced through line 17. On the other hand, the inert gas separated in the inert gas separation space 18 in the urea synthesis autoclave 1 is withdrawn from line 19 along with the accompanied carbon dioxide and ammonia is depressurized to 10–25 kg/cm$^2$ gauge by the reducing value 20, and is introduced in between the middle and bottom of high pressure absorber 16. At the bottom of high pressure absorber 16, a cooler 21 is fitted to maintain the bottom temperature of high pressure absorber at a temperature of from 100° to 130° C. In the cooler 21, recovery of heat of absorption may, of course, be performed by means of the production of steam. However, a urea slurry resulting from the concentration crystallizer for the aqueous urea solution is most preferably introduced into the cooler 21 as a cooling medium for cooling. Thus, the heat developed due to the recovery of carbon dioxide and ammonia introduced into the high pressure absorber along with the inert gas entrained therein can readily and effectively be recovered without any additional apparatuses.

The gaseous mixture introduced from line 17 and line 19A is brought into contact with the absorbate introduced from line 15 and an aqueous ammonia introduced from line 31 as described later to absorb all of carbon dioxide and a portion of ammonia in the gaseous mixture. Unabsorbed ammonia is passed along with the inert gas from the top of the absorber into the ammonia condenser through line 22, and water-cooled for condensation. A portion of the liquid ammonia thus obtained is recycled to the top of high pressure absorber for cooling through line 24, and the balance is recycled to the urea synthesis autoclave 1 through line 25.

The inert gas separated from liquid ammonia in the ammonia condenser 23 is introduced into the ammonia washing column 27 along with ammonia gas entrained therein through line 26, washed with water introduced from line 28 to remove ammonia therefrom, withdrawn through line 29, depressurized to atmospheric pressure by the reducing value 30, and withdrawn through line 29A for proper applications. At the bottom of the ammonia washing column 27 a cooler (not shown) is fitted. The aqueous ammonia withdrawn from the bottom of the ammonia washing column 27 is passed to the top of high pressure absorber 16 through line 31. The inert gas contains oxygen added as a corrosion inhibitor for the apparatus as well as hydrogen, methane, and the like, so that the inert gas in line 19 after removing ammonia may have some danger of explosion. However, it can be said that it has little or no danger of explosion because the pressure therein is in the range of from 10 to 25 kg/cm$^2$ gauge. However, even if an explosion should occur therein, it would inflict no damage on the main line, because the inert gas in line 29 is isolated from the main line through the ammonia washing column 27.

The high pressure absorbate withdrawn from the bottom of high pressure absorber 16 is, via line 32, pressurized to the same pressure as the pressure of stripper by the pump 33 to be introduced to the top of the carbamate condenser 34. On the other hand, a gaseous mixture of unreacted carbon dioxide and ammonia resulting from stripper 6 is passed to the top of carbamate condenser 34 through line 35 and brought into contact with the high pressure absorbate to condense at least a part thereof to form ammonium carbamate solution. The heat generated therein is removed and recovered by cooling with water introduced from line 36. From line 37, steam produced from the heat thus recovered and having a pressure of from 3 to 10 kg/cm$^2$ gauge is withdrawn. The temperature of carbamate condenser 34 is maintained at a temperature of from 140° to 200° C. due to the production of steam. The ammonium carbamate solution thus formed as well as uncondensed carbon dioxide and ammonia, if any, is introduced into urea synthesis autoclave 1 through line 4.

The process for synthesizing urea of the present invention has various advantages as described below. Firstly, the separation for recovery of considerable portion of unreacted carbon dioxide and ammonia by stripping with carbon dioxide or ammonia under a pressure approximately equal to the urea synthesis pressure makes it possible to decrease the amount of the absorbent used for recovery thereof, to decrease the amount of the absorbent introduced into the urea synthesis autoclave, and consequently to obtain a high conversion ratio. Secondly, the withdrawal of the inert gas accumulated within the urea synthesis system due to the inert gas in the make-up carbon dioxide and ammonia and also containing oxygen added thereto as corrosion inhibitor for the apparatuses is effected either in the urea synthesis stage or between the urea synthesis stage and the stripping stage, so that the amount of carbon dioxide and ammonia entrained in the inert gas thus withdrawn remains at a low level. Thirdly, according to the present invention there are provided the high pressure distillation and absorption stages after the stripping stage, so that the recovery of carbon dioxide and ammonia accompanied by the aforesaid inert gas can be performed along with heat recovery in the high pressure absorption stage. Moreover, the pressure in the above stage is in the range of from 10 to 25 kg/cm² gauge, the inert gas, from which carbon dioxide and ammonia have been removed, has little or no danger of explosion.

An example in accordance with a process illustrated by the accompanying drawing is shown below. The example shows the amount and composition of the stream in each line as well as operation conditions in each apparatus.

EXAMPLE

| Apparatus or Stream | Operation conditions | | Stream | | | | |
|---|---|---|---|---|---|---|---|
| | Temperature (°C.) | Pressure (kg/cm²G) | Urea (kg/hr) | $CO_2$ (kg/hr) | $NH_3$ (kg/hr) | $H_2O$ (kg/hr) | Inert gas (Nm³/hr) |
| 2A | | | | | 638 | | 3.0 |
| 3A | | | | 15 | | | 7.0(*) |
| 4 | | | 120 | 1083 | 1127 | 244 | |
| 1 | 200 | 250 | | | | | |
| 5A | | | 1140 | 334 | 1163 | 548 | |
| 6 | 195 | 250 | | | | | |
| 10A | | | 1140 | 200 | 300 | 460 | |
| 12 | 170 | 17 | | | | | |
| 14 | | | 1140 | 60 | 95 | 435 | |
| 15 | | | 120 | 58 | 94 | 114 | |
| 16 | 103 | 16.5 | | | | | |
| 17 | | | | 140 | 205 | 25 | |
| 19A | | | | 16 | 24 | 2 | |
| 21 | [Being cooled by heat exchange with aqueous urea solution. The amount of heat recovered corresponds to 0.2 part of stream per part of urea.] | | | | | | |
| 22 | | | | | 190 | | 10 |
| 24 | | | | | 102 | | |
| 25 | | | | | 59 | | |
| 26 | | | | | 29 | | 10 |
| 31 | | | | | 29 | 15 | |
| 32A | | | 120 | 214 | 264 | 156 | |
| 34 | 175 | 250 | | | | | |
| 35 | | | | 869 | 863 | 88 | |
| 37 | [0.65 parts of steam of 5 kg/cm² G] | | | | | | |

(*)Containing air as corrosion inhibitor

What is claimed is:

1. In a process for synthesizing urea including reacting carbon dioxide and ammonia in a stoichiometrical excess thereto at urea synthesis pressures and temperatures to form a urea synthesis effluent containing unreacted carbon dioxide and ammonia, separating an inert gas from said urea synthesis effluent along with said unreacted carbon dioxide and ammonia entrained in the inert gas under a pressure approximately equal to the urea synthesis pressures, subjecting said urea synthesis effluent to stripping with carbon dioxide or ammonia under a pressure approximately equal to the urea synthesis pressures to separate at least a part of said unreacted carbon dioxide and ammonia, subjecting the urea synthesis effluent resulting from said stripping to high pressure distillation under a pressure of from 10 to 25 kg/cm² gauge to separate the major portion of carbon dioxide and ammonia contained therein, subjecting the urea synthesis effluent resulting from said high pressure distillation to low pressure distillation to separate all of the carbon dioxide and ammonia contained therein, to obtain an aqueous urea solution, producing urea from the aqueous urea solution thus obtained, absorbing said carbon dioxide and ammonia separated in said high pressure distillation in an absorbent to form a high pressure absorbate, cooling unabsorbed ammonia gas to separate resulting liquid ammonia from said inert gas, contacting said unreacted carbon dioxide and ammonia separated in said stripping with said high pressure absorbate for condensation, and recycling an ammonium carbamate solution thus obtained and said liquid ammonia to said urea synthesis, the improvement which comprises contacting said inert gas accompanying unreacted carbon dioxide and ammonia with said absorbent along with said carbon dioxide and ammonia separated in said high pressure distillation to obtain said inert gas substantially free of carbon dioxide and containing unabsorbed ammonia, cooling the resulting inert gas to separate said inert gas from the resulting liquid ammonia, and discharging the inert gas thus separated.

2. A process as claimed in claim 1, wherein said inert gas separated from said liquid ammonia is washed with water to absorb and remove substantially all of the ammonia contained therein.

3. A process as claimed in claim 1, wherein the molar ratio of said ammonia as starting material to said carbon dioxide as starting material is in the range of from 2.1 to 5, said urea synthesis pressure is of from 100 to 300 kg/cm² gauge, and said urea synthesis temperature is of from 170° to 220° C.

4. A process as claimed in claim 1, wherein said stripping is effected with the carbon dioxide as starting material under a pressure of from 90 to 310 kg/cm² gauge at a temperature of from 150° to 230° C.

5. A process as claimed in claim 1, wherein the carbon dioxide and ammonia resulting from said low pressure distillation is absorbed in said absorbent beforehand.

* * * * *